(12) United States Patent
Moloy

(10) Patent No.: US 8,067,329 B2
(45) Date of Patent: Nov. 29, 2011

(54) BORON-BASED CATALYSTS

(75) Inventor: Kenneth Gene Moloy, Hockessin, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 70 days.

(21) Appl. No.: 12/432,827

(22) Filed: Apr. 30, 2009

(65) Prior Publication Data

US 2010/0279852 A1 Nov. 4, 2010

(51) Int. Cl.
*B01J 21/02* (2006.01)

(52) U.S. Cl. .................... 502/202; 502/203; 502/164

(58) Field of Classification Search .................... 502/164
See application file for complete search history.

(56) References Cited

U.S. PATENT DOCUMENTS

| | | | |
|---|---|---|---|
| 2,976,307 A | 11/1959 | Rudner et al. | |
| 3,007,970 A | 11/1961 | Ashby | |
| 5,608,116 A | 3/1997 | Halling et al. | |
| 6,335,423 B1 | 1/2002 | Varma | |
| 6,352,798 B1 * | 3/2002 | Lee et al. ...................... | 429/324 |
| 7,256,152 B2 * | 8/2007 | Olivier-Bourbigou et al. ............................. | 502/150 |
| 7,473,492 B2 * | 1/2009 | Okumura et al. ............. | 429/317 |
| 2004/0034253 A1* | 2/2004 | Angell et al. ..................... | 568/6 |
| 2005/0004404 A1 | 1/2005 | Muller et al. | |
| 2005/0256331 A1 | 11/2005 | Der Puy et al. | |
| 2006/0069220 A1 | 3/2006 | Meurs et al. | |

FOREIGN PATENT DOCUMENTS

| | | | |
|---|---|---|---|
| JP | 07207017 A | * | 8/1995 |
| WO | 9705944 A1 | | 2/1997 |

OTHER PUBLICATIONS

R. E. Davis et al., Boron Hydrides V. Methanolysis of Sodium Borohydride, J. Am Chem Soc., 1962, V. 84, pp. 895-898.
J. H. Golden et al., Disproportionation of Alkoxyborohydrides: A 11B NMR Study of the Reaction Between Sodium Borohydride and Fluorinated Alcohols and Phenols. The Preparation of Tris(Fluoroalkoxy)- and Tris(Fluoropenoxy)Borohydrides, Inorg. Chem., 1992, vol. 31, pp. 1533-1535.
A. G. Campana et al., Sodium Tetramethoxyborate: An Efficient Catalyst for Michael Additions of Stabilized Carbon Nucleophiles, J. Org. Chem., 2007, vol. 72, pp. 8127-8810.
US 7,314,686, 01/2008, Angell et al. (withdrawn)

* cited by examiner

*Primary Examiner* — Melvin Mayes
*Assistant Examiner* — Melissa Stalder

(57) ABSTRACT

Boron based catalysts and processes for preparing the catalysts are provided. The catalysts are suitable for the alkoxylation of alcohols using alkylene epoxides.

9 Claims, No Drawings

BORON-BASED CATALYSTS

RELATED APPLICATIONS

This application is related to copending application Ser. No. 12/432,814 and copending application Ser. No. 12/432,821, filed on the same date as this application.

FIELD OF INVENTION

The present invention is directed to boron based catalysts, and processes to prepare them. The catalysts are suitable for the alkoxylation of alcohols using alkylene epoxides.

BACKGROUND

Alcohol alkoxylate containing materials have been used in a wide variety of industrial applications, for example as non-ionic surfactants. They are typically prepared by the reaction of an alcohol with an alkylene epoxide such as ethylene oxide (i.e. oxirane) or propylene oxide (i.e. 2-methyoxirane) in the presence of one or more catalysts. Fluorinated alkylalkoxylates which are prepared by the reaction of an alcohol incorporating a fluorinated alkyl group with an alkylene epoxide are an important class of materials. Fluorinated alkylalkoxylates are especially useful in several industrial applications, including use as nonionic surfactants in the manufacture of PVC films, electrochemical cells, and various photographic coatings.

Known catalyst systems and processes for the alkoxylation of fluorinated alcohols include using Lewis acids such as boron trifluoride or silicon tetrafluoride, alone in combination with metal hydrides, fluorides, alkyls or alkoxides. Such acidic materials also catalyze side reactions such as dimerization of alkylene epoxides to form dioxanes during the alkylalkoxylation. For this reason many processes use strongly basic catalysts to alkoxylate alcohols. However, some alcohols are not stable to strong base. For instance, in the presence of strong base some hydrofluorocarbons are prone to elimination of HF and the formation of fluorinated olefins. Halohydrins, $XCR_2CR_2OH$, are well known to form epoxides in the presence of base and are used for this purpose synthetically to convert olefins to epoxides.

Halling and Huang in U.S. Pat. No. 5,608,116 disclose a process for the preparation of fluoralkylalkoxylates in which a commercial mixture of perfluoroalkylethanols having the general structure $R_fCH_2CH_2OH$ are alkoxylated in the presence of a catalyst system comprising an iodine source and alkali metal borohydride such as $NaBH_4$, an expensive material that presents safety concerns due to flammability.

SUMMARY

One aspect of the invention is a composition comprising a compound $MB(OR^7)_x(X)_{4-x}$ wherein: $R^7$ is a linear, branched, cyclic, acyclic, or aromatic hydrocarbyl group, optionally substituted, having from 2 to 20 carbon atoms; X is fluoride, bromide, or iodide; M is a cation of the alkali metals $Na^+$, $K^+$, $Li^+$ or a cation of the type $R^2R^3R^4R^5N^+$ or $R^2R^3R^4R^5P^+$ where $R^2$, $R^3$, $R^4$, and $R^5$ independently are hydrocarbyl groups of 1 to 20 carbon atoms; and x is 1 to 4.

Another aspect of the present invention is a process for preparing a compound $MB(OR^7)_x(X)_{4-x}$ where x is 1-3, comprising combining $B(OR^7)_3$ and MX in a suitable solvent, wherein the $B(OR^7)_3$ and MX are combined in a molar ratio of from about 1:3 to about 3:1.

DETAILED DESCRIPTION

As used herein, the term "hydrocarbyl" means a straight chain, branched or cyclic arrangement of carbon atoms connected by single, double, triple, or aromatic carbon to carbon bonds and/or by ether linkages, and substituted accordingly with hydrogen atoms. Such hydrocarbyl groups may be aliphatic and/or aromatic. Examples of hydrocarbyl groups include methyl, ethyl, propyl, isopropyl, butyl, isobutyl, t-butyl, cyclopropyl, cyclobutyl, cyclopentyl, methylcyclopentyl, cyclohexyl, methylcyclohexyl, benzyl, phenyl, o-tolyl, m-tolyl, p-tolyl, xylyl, vinyl, allyl, butenyl, cyclohexenyl, cyclooctenyl, cyclooctadienyl, and butynyl.

"Optional" or "optionally" means that the subsequently described event or circumstance may or may not occur, and that the description includes instances where said event or circumstance occurs and instances where it does not. For example, the phrase "optionally substituted" means that moiety may or may not be substituted and that the description includes both unsubstituted moieties and unsubstituted moieties.

When a group or moiety is referred to herein as being "substituted" it means that the group or moiety contains one or more substituent groups that are inert under the process conditions to which the compound containing these groups is subjected (e.g., an inert functional group, see below). The substituent groups can be attached pendant to the original moiety or may replace one or more atoms of the moiety. The substituent groups also do not substantially detrimentally interfere with the process described herein. Included in the meaning of "substituted" are chains or rings containing one or more heteroatoms, such as nitrogen, oxygen and/or sulfur. In a substituted hydrocarbyl, all of the hydrogens may be substituted, as in trifluoromethyl.

By "inert functional group" is meant a group other than hydrocarbyl or substituted hydrocarbyl that is inert under the process conditions to which the compound containing the group is subjected. The functional groups also do not substantially interfere with any process described herein that the compound in which they are present may take part in. Examples of functional groups include halo (fluoro, chloro, bromo and iodo), and ether.

By "alkyl" is meant a monovalent hydrocarbyl group containing only single bonds.

By "alkylene" is meant a divalent hydrocarbyl group containing only single bonds.

By "fluorinated" is meant that at least one hydrogen that is bonded directly to a carbon has been replaced with a fluorine.

By "fluoroalkyl" is meant an alkyl group that is partially or totally fluorinated.

Described herein is a process for the preparation of alkyl alkoxylates, especially fluoroalkyl alkoxylates via epoxidation, using a boron-based catalyst. The catalyst can be used with a large variety of alcohols.

In one embodiment, the process comprises: contacting one or more alcohols of the formula $R^1OH$ with one or more 1,2 alkylene epoxides of the formula Q(O), wherein Q is a linear alkylene group of the formula $C_yH_{2y}$, where y is an integer from 2 to 10, and $R^1$ is a linear, branched, cyclic, or aromatic hydrocarbyl group, optionally substituted, having from 1 to 30 carbon atoms; at a temperature from about 60° C. to about 200° C. and a pressure from ambient atmospheric pressure to about 1035 KPa; in the presence of a catalyst at a molar ratio of alcohol to catalyst of from about 200 to 15, wherein the catalyst is $MB(OR^1)_x(X)_{4-x}$ or $B(OR^1)_3/MX$ where M is $Na^+$, $K^+$, $Li^+$, $R^2R^3R^4R^5N^+$, or $R^2R^3R^4R^5P^+$ and $R^2$, $R^3$, $R^4$, and $R^5$ independently are hydrocarbyl groups, and x is 1 to 3; to form an alkyl alkoxylate of the formula $R^1O(QO)_mH$ where m is from 1 to 20.

$R^1$ can be an alkyl group with from 1 to 30 carbon atoms, or an aromatic group such as phenyl. $R^1$ can be optionally substituted with functionalities such as but not limited to ether, amide, ester, halogen, sulfur, nitrile, with the proviso that the functional group does not interfere with the alkoxylation reaction. It can also be partially fluorinated or a linear fluoroalkyl group of the type $C_yF_{2y+1}CH_2CH_2$ where y is an integer from 2 to 20. $R^1$ can be a mixture of one or more alkyl groups, such as a mixture of fluoroalkyl groups.

In one embodiment a mixture of alcohols of the formula $R^1OH$ can be contacted with the 1,2-alkylene epoxides in the process, to produce a corresponding mixture of alkyl alkoxylates, which can be a telomeric mixture. The 1,2 alkylene epoxide of the formula Q(O) can be ethylene oxide, propylene oxide, 1,2-butylene oxide, 2,3-butylene oxide, and styrene oxide, or a mixture thereof, and typically can be ethylene oxide or propylene oxide.

Catalysts suitable for the processes disclosed herein include $MB(OR^1)_x(X)_{4-x}$ or $B(OR^1)_3/MX$. By $B(OR^1)_3/MX$ is meant a two component catalyst which is a mixture of $B(OR^1)_3$ and MX. The two components can be added separately, in any order, or simultaneously, to the process. $R^1$ is as defined above. In the formula $MB(OR^1)_x(X)_{4-x}$ x can be 1 to 3 but is typically 3. It is believed that the $B(OR^1)_3/MX$ catalyst forms a composition of the formula $MB(OR^1)_3X$ in situ, which serves as the catalytic species. $R^1$ is as defined above.

M is a cation of the alkali metals $Na^+$, $K^+$, $Li^+$ or a cation of the type $R^2R^3R^4R^5N^+$ or $R^2R^3R^4R^5P^+$ where $R^2$, $R^3$, $R^4$, and $R^5$ independently are hydrocarbyl groups of 1 to 20 carbon atoms. Typically, $R^2$, $R^3$, $R^4$, and $R^5$ independently are alkyl groups of from 1 to 4 carbons, such as butyl, and can be the same or different. In one embodiment, M is $R^2R^3R^4R^5N^+$.

X is fluoride, bromide, or iodide, but is typically I.

The catalysts can be obtained commercially or prepared by any method known in the art, such as the methods disclosed herein below.

In one embodiment, the process includes contacting an alcohol with an alkylene oxide in the presence of a catalyst. The alcohol and catalyst can be added to the alkylene oxide either simultaneously or in any order. Typically the catalyst is either added to, or generated in, the neat alcohol, which also serves as a solvent for the reaction. One or more co-solvents may be additionally used, provided that the solvent or solvents are substantially inert to all reagents and products. The catalyst and alcohol reaction mixture is then treated with the alkylene oxide at elevated temperature until the desired conversion is achieved.

The catalyst is used in an amount relative to the alcohol of from about 0.1 mole % to about 11 mole %, typically about 0.5% to about 8%, more typically about 1 mole % to about 6%. The alkylene oxide is typically fed to the catalyst/alcohol solution as a liquid or vapor after the addition of the catalyst and alcohol. The amount of alkylene oxide added to the reaction mixture is not critical other than providing the minimum amount necessary to provide the desired number of alkyloxy units in the final product.

The amount of alkylene oxide used is variable, and is determined by the physical properties desired in the alkoxylated alcohol product. Thus, in some cases the average number of alkoxy groups per starting alcohol may need to be relatively low, e.g., 2 to 6, while for other cases a significantly higher number may be required such as from 8 to 30 or more.

The process is typically performed under inert atmosphere, such as nitrogen or another inert gas, for safety reasons owing to the flammability of many alkylene oxides. It is typical to run the process under anhydrous conditions since water will usually be alkoxylated, thereby producing contaminants. Water may also inhibit or poison some catalysts.

The reaction temperature is variable and can range from about 60° C. to about 180° C., and preferably is from about 80° C. to 140° C. The desired temperature is primarily determined by the reaction times that can be tolerated, lower temperatures giving longer reaction times, and higher temperatures giving shorter reaction times.

The reaction is run at the pressure generated during the reaction, typically about 0 to about 200 psig, or about 0 to about 100 psig.

Agitation is not required, but is usually provided to facilitate a homogeneous mix and to facilitate heat transfer.

The alkyl alkoxylates produced by the processes disclosed herein can have any desired number of alkyloxy units, allowing the tailoring of properties for the desired end use. The alkyloxy units will typically be present at about 10% to about 90% by weight of the alkyl alkoxylate composition; more typically about 20% to about 70%.

In one embodiment, the process forms a telomeric mixture, also known as a telomer. A telomer is formed when a taxogen (C) is added to a telogen (AB) by application so that a mixture is formed of polymers of low polymerization degree represented by the formula: $A(C)_mB$ (wherein m is generally in the range of 1 to 20). As used herein, a telomeric mixture is defined as a plurality of telomers whose polymerization degree m are different from each other. Thus, in some embodiments the processes disclosed herein can produce a telomeric mixture of alkyl alkoxylates of the formula $R^1O(QO)_mH$, having different values of m. The processes described herein are particularly suitable for the production of telomers with an average degree of polymerization of 1-20, more typically 2-8.

The process can optionally further comprise the recovery or isolation of one or more of the alkyl alkoxylates produced. This can be done by any method known in the art, such as distillation, decantation, recrystallization, or extraction.

Also provided, is a compound comprising $MB(OR^7)_x(X)_{4-x}$ wherein $R^7$ is a linear, branched, cyclic, acyclic, or aromatic hydrocarbyl group, optionally substituted, having from 2 to 20 carbon atoms; X is fluoride, bromide, or iodide; M is a cation of the alkali metals $Na^+$, $K^+$, $Li^+$ or a cation of the type $R^2R^3R^4R^5N^+$ or $R^2R^3R^4R^5P^+$ where $R^2$, $R^3$, $R^4$, and $R^5$ independently are hydrocarbyl groups of 1 to 20 carbon atoms; and x is 1 to 4.

The compounds can be used as catalysts, particularly in alkoxylation reactions.

$R^7$ can be an alkyl group with from 1 to 30 carbon atoms, or an aromatic group such as phenyl. It can be optionally substituted with functionalities such as but not limited to ether, amide, ester, halogen, sulfur, nitrile, with the proviso that the functional group does not interfere with the alkoxylation reaction. It can also be partially fluorinated or a linear fluoroalkyl group of the type $C_yF_{2y+1}CH_2CH_2$ where y=from 2 to 20, especially when x is 4. $R^7$ can be a mixture of groups, such as a mixture of fluoroalkyl groups. When x is 4, $R^7$ can be a fluorinated alkyl, either partially or totally fluorinated.

In the formula $MB(OR^7)_x(X)_{4-x}$ x can be 1 to 3 but is typically 3.

M is a cation of the alkali metals $Na^+$, $K^+$, $Li^+$ or a cation of the type $R^2R^3R^4R^5N^+$ or $R^2R^3R^4R^5P^+$ where $R^2$, $R^3$, $R^4$, and $R^5$ independently are hydrocarbyl groups of 1 to 20 carbon atoms. Typically, $R^2$, $R^3$, $R^4$, and $R^5$ independently are alkyl groups of from 1 to 4 carbons, such as butyl, and can be the same or different. In one embodiment, M is $R^2R^3R^4R^5N^+$.

X is fluoride, bromide, or iodide, but is typically iodide.

When x is 4, the tetraalkoxy borates $B(OR)_4^-$ can be prepared by a variety of methods. For instance, a two-step process starting from $B(OH)_3$ is described by Malkowsky in European Journal of Inorganic Chemistry 2006, page 1690. The compounds can also be prepared by an alcohol exchange using, for instance, $B(OMe)_4^-$ or other tetraalkoxides. Additionally, $NaBO_2$ or other anionic borates can react with alcohols with water removal to yield the tetraalkoxides as shown:

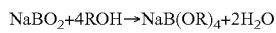

$$NaBO_2 + 4ROH \rightarrow NaB(OR)_4 + 2H_2O$$

The compounds $MB(OR)_x(X)_{4-x}$ where x is from 1 to 3 can be prepared by combination of the neutral borate esters $B(OR)_3$ with $M^+X^-$. The $B(OR)_3$ can be formed in a first step followed by the addition of MX in a second step. Alternatively, $MB(OR)_x(X)_{4-x}$ can be generated in a single step by combination of MX and either $B(OH)_3$ or $B_2O_3$ in the alcohol ROH and then optionally removing water.

$B(OR)_3$ can be prepared by reaction of $B(OH)_3$ or $B_2O_3$ and HOR with elimination of water. Alternatively, they can be prepared from a boron halide such as $BCl_3$ and an alcohol with the formation of HCl. The HCl generated is removed with a base. The $B(OR)_3$ compounds can be prepared independently or generated in the same reactor in which the alkoxylation is to be performed. Water removal is optional but is typically performed to avoid the formation of poly(alkylene glycols), which are formed by the alkoxylation of water. If the presence of poly(alkylene glycols) in the alcohol alkoxylate product is unacceptable, then water should be removed prior to performing the alkoxylation reaction.

EXAMPLES

The following abbreviations were used: "L" means liter, "mol" means mole, "mL" means milliliter, "%" means percent, "ca." means approximately, "g" means gram, "h" means hour, "EO" means ethylene oxide.

All $B(OR)_3$ compounds were prepared by previously published methods such as that described in Cotton, F. A.; Wilkinson, G. "Advanced Inorganic Chemistry, Fifth Edition", Wiley-Interscience: New York, 1988, p 168 and p 171. Malkowsky, et al., Eur. J. Inorg. Chem. 2006, 1690 where a oxyboron species such as $B(OH)_3$ or $B_2O_3$ are reacted with the appropriate alcohol. The reactions proceeded rapidly in a solvent, typically refluxing toluene. Water was removed continuously by standard methods to ensure complete conversion of the oxyboron material to the ester $B(OR)_3$. These compounds were characterized by multinuclear NMR(1H, 13C, 19F), mass spectrometry, and elemental analysis. The following is a representative reaction.

Example 1

$B(OCH_2CH_2C_6F_{13})_3$ $B_2O_3$ (1.60 g finely ground powder, 46.0 mmol) and 52.8 g (145 mmol, 3.15 eq) $HOCH_2CH_2C_6F_{13}$ were combined in 75 mL toluene. The mixture was refluxed under nitrogen and a Dean Stark trap was used to remove water. Water evolution appeared to be complete after ca. 1 h; reflux was continued another 2 h to ensure complete reaction. The water collected totaled 1.2 mL, 100% of theory. The product was filtered and then stripped on the rotovap to yield the product as a colorless liquid. Yield: 50.36 g, 100%.

NMR showed the product to contain ca. 94% $B(OR_f)_3$ and 6% $HOR_f$. $^1H$ NMR (d8-THF): 4.15 (t, 6.3 Hz, 6H), 2.47 (tt, 19.0 Hz, 6.2 Hz, 6H).

NMR Characterization of $F^- + B(OR)_3$

To a solution of $B(OCH_2CH_2CF_2CH_2C_4F_9)_3$ (0.189 g, 0.19 mmol) in 2 mL of diethyl ether was added a slurry of $Bu_4NF$ monohydrate (0.062 g, 0.22 mmol) in 2 mL of ether. After a few minutes of stirring the crystalline $Bu_4NF$ dissolved to give a colorless solution. After stirring overnight the ether was stripped under vacuum. The resulting oil was redissolved in $CD_2Cl_2$ and examined by $^{19}F$ NMR, which showed a 1:1:1:1 quartet (−144.9 ppm, $J_{B-F}$=17.3 Hz), diagnostic of a fluoro-boron species and assigned to the anion $B(OCH_2CH_2CF_2CH_2C_4F_9)_3F^-$.

This demonstrates the formation of $B(OR)_3X^-$ upon combination of $B(OR)_3$ and $X^-$ in solution.

Example 2

Synthesis of $NaB(OR)_4$

These compounds were prepared from the reaction of $NaB(OCH_3)_4$ with the appropriate alcohol. Methanol is liberated from this reaction and is removed by heating the reaction mixture under vacuum or a nitrogen purge. The compounds were characterized by elemental analysis and $^1H$ NMR. The following is representative.

$NaB(OCH_3)_4$ (1.00 g, 6.3 mmol) and $HOCH_2CH_2OCF_2CFHOCF_2CF_2CF_3$ (9.35 g, 28.5 mmol) were combined and heated at 70° C. to give a pale yellow liquid. After 3 h the mixture was cooled to room temperature and the evolved methanol was removed under vacuum. The product was then heated at 100° C. under vacuum for 2 h. The product was washed several times with ether and dried.

$^1H$ NMR ($CD_3OD$): In addition to resonances due to $HOCH_2CH_2OCF_2CFHOCF_2CF_2CF_3$ a small amount of residual $HOCH_3$ (3 mol %) was detected.

Elemental analysis: Calcd for $C_{28}H_{20}BF_{40}NaO_{12}$ C: 25.06%; H, 1.50%; F, 56.62%. Found: C, 24.80%; H, 1.63%; F, 56.58%.

Comparative Example 1

Treatment of $C_6F_{13}CH_2CH_2OH$ with NaH

A vial was charged 0.259 g (0.71 mmol) of $C_6F_{13}CH_2CH_2OH$, 4 mg (0.17 mmol) of NaH, and a stir bar. Gas evolution occurred immediately. The mixture was heated, with stirring, to 100° C. The initially colorless solution turned dark yellow-brown. After 75 min the mixture was cooled to room temperature. GCMS analysis showed, in addition to unreacted alcohol, a new peak with mass 344 corresponding to loss of HF (mass=20) from the alcohol (mass=364). 1H NMR analysis ($CDCl_3$) showed olefinic resonances assignable to $C_5F_{11}CF$=$CHCH_2OH$ in addition to other minor olefin products. This example shows that the method of treating an alcohol with sodium hydride to generate an alkoxide ethoxylation catalyst fails for a fluorinated alcohol prone to elimination of fluoride and formation of olefin.

Comparative Example 2

Treatment of $C_6F_{13}CH_2CH_2OH$ with KOH

A vial was charged with 0.251 g (0.69 mmol) of $C_6F_{13}CH_2CH_2OH$, 12 mg (0.21 mmol) of KOH, and a stir bar. The mixture was heated, with stirring, to 100° C. The initially colorless mixture turned dark yellow-brown. After 75 min the mixture was cooled to room temperature. GCMS analysis showed, in addition to unreacted alcohol, a new peak with mass 344 corresponding to loss of HF (mass=20) from the alcohol (mass=364). 1H NMR analysis (CDCl$_3$) showed olefinic resonances assignable to $C_5F_{11}CF=CHCH_2OH$ in addition to other minor olefin products.

This example shows that the method of treating an alcohol with potassium hydroxide to generate an alkoxide ethoxylation catalyst fails for a fluorinated alcohol prone to elimination of fluoride and formation of olefin.

Examples 3-34

Ethoxylation Reactions

General Procedure

Ethoxylations were performed in a stainless steel reactor. In some cases a glass liner was used. The reactor was charged with the alcohol, a magnetic stir bar, catalyst components (MB(OR)$_4$ or B(OR)$_3$ and MX), sealed, and then connected to a gas manifold. When the catalyst was of the form B(OR$_1$)$_3$/MX, both components were added together. The reactor was evacuated and then a premeasured amount of EO, in a ratio of EO/alcohol of 4 to 10, was condensed into the reactor at 0-5° C. When the EO transfer was complete the system was backfilled with ca. 1 psig nitrogen and the feed valves closed. The reactor was placed in a block heater and brought to reaction temperature and stirred magnetically. Reaction progress was followed by monitoring the pressure. At the higher catalyst concentrations (ca. 6 mole %) gas uptake was normally complete within 3-6 hours. Lower catalyst concentrations required longer times and were typically allowed to proceed overnight to ensure complete ethylene oxide consumption.

For analysis and work up the reactor was cooled to 0-3° C. with ice. Unreacted EO, if present, was removed by vacuum and collected in a −196° C. trap. The ethoxylate product was analyzed by GC and various other techniques (HPLC, MS, NMR).

Ethoxylation results are summarized in the attached table. "EO#" is the average number of ethylene oxide units inserted, e.g., the average number of n in the formula RO(CH$_2$CH$_2$O)$_n$H. The value for n for a given ethoxylation reaction is generally determined by the alcohol conversion and the ratio of ethylene oxide to alcohol.

TABLE 1

| Ex. | Alcohol | Catalyst | Catalyst mole % | Temp. ° C. | Initial Pressure psig | Unreacted alcohol, % | Alcohol Conversion, % | EO# |
|---|---|---|---|---|---|---|---|---|
| 3 | $C_6F_{13}CH_2CH_2OH$ | NaB(OCH$_2$CH$_2$C$_6$F$_{13}$)$_4$ | 4.3 | 120 | 215 | 1.7 | 98.3 | 8 |
| 4 | $C_6F_{13}CH_2CH_2OH$ | NaB(OCH$_2$CH$_2$C$_6$F$_{13}$)$_4$ | 5.1 | 120 | 155 | 1.4 | 98.6 | 6 |
| 5 | $C_nF_{2n+1}CH_2CH_2OH$, n = 6-14 (mixture of alcohols) | NaB(OCH$_2$CH$_2$CnF$_{2n+1}$)$_4$ (n = 6-14 mixture) | 3.9 | 120 | 180 | 1 | 99 | 8 |
| 6 | $C_6F_{13}CH_2CH_2OH$ | B(OCH$_2$CH$_2$C$_6$F$_{13}$)$_3$ Bu$_4$NF | 10.2 9.8 | 120 | 60 | 8 | 92 | 3 |
| 7 | $C_6F_{13}CH_2CH_2OH$ | B(OCH$_2$CH$_2$C$_6$F$_{13}$)$_3$ NaI | 4.6 4.7 | 120 | 60 | 5 | 95 | 5 |
| 8 | $C_6F_{13}CH_2CH_2OH$ | B(OCH$_2$CH$_2$C$_6$F$_{13}$)$_3$ NaI | 4.6 5.1 | 120 | 60 | 5 | 95 | 4 |
| 9 | $C_6F_{13}CH_2CH_2OH$ | B(OCH$_2$CH$_2$C$_6$F$_{13}$)$_3$ Bu$_4$NI | 4.8 4.7 | 120 | 60 | 2.5 | 97.5 | 6 |
| 10 | $C_6F_{13}CH_2CH_2OH$ | B(OCH$_2$CH$_2$C$_6$F$_{13}$)$_3$ Bu$_4$NI | 4.7 4.4 | 120 | 60 | 3.5 | 96.5 | 6 |
| 11 | $C_4F_9CH_2CF_2CH_2CH_2OH$ | B(OCH$_2$CH$_2$CF$_2$CH$_2$C$_4$F$_9$)$_3$ Bu$_4$NI | 5.6 5.2 | 120 | 100 | 11 | 89 | 4 |
| 12 | $C_4F_9CH_2CF_2CH_2CH_2OH$ | B(OCH$_2$CH$_2$CF$_2$CH$_2$C$_4$F$_9$)$_3$ Bu$_4$NI | 5.6 5.8 | 105 | 60 | 0.3 | 99.7 | 6 |
| 13 | $C_4F_9CH_2CF_2CH_2CH_2OH$ | B(OCH$_2$CH$_2$CF$_2$CH$_2$C$_4$F$_9$)$_3$ Bu$_4$NBr | 6.1 6.8 | 120 | 60 | 0.2 | 99.8 | 5 |
| 14 | $C_4F_9CH_2CF_2CH_2CH_2OH$ | B(OCH$_2$CH$_2$CF$_2$CH$_2$C$_4$F$_9$)$_3$ Bu$_4$NBr | 6.1 3.2 | 120 | 60 | 1.8 | 98.2 | 4 |
| 15 | $C_4F_9CH_2CF_2CH_2CH_2OH$ | B(OCH$_2$CH$_2$CF$_2$CH$_2$C$_4$F$_9$)$_3$ Bu$_4$NI | 6.1 6.3 | 120 | 60 | 0.4 | 99.6 | 5-6 |
| 16 | $C_4F_9CH_2CF_2CH_2CH_2OH$ | B(OCH$_2$CH$_2$CF$_2$CH$_2$C$_4$F$_9$)$_3$ Bu$_4$NI | 6.1 3.2 | 120 | 60 | 0.7 | 99.3 | 5-6 |
| 17 | $C_6F_{13}CH_2CH_2OH$ | B(OCH$_2$CH$_2$C$_6$F$_{13}$)$_3$ Bu$_4$NI | 4.1 4.1 | 105 | 60 | 0.04 | 99.96 | 6 |
| 18 | $C_6F_{13}CH_2CH_2OH$ | B(OCH$_2$CH$_2$C$_6$F$_{13}$)$_3$ Bu$_4$NI | 1.1 1.1 | 105 | 85 | 0.04 | 99.96 | 6 |
| 19 | $C_6F_{13}CH_2CH_2OH$ | B(OCH$_2$CH$_2$C$_6$F$_{13}$)$_3$ NaI | 1.9 2.0 | 105 | 115 | 1.4 | 98.6 | 6 |
| 20 | $C_4F_9CH_2CH_2OH$ | NaB(OCH$_2$CH$_2$C$_4$F$_9$)$_4$ | 4.0 | 120 | 150 | 4 | 96 | 2 |
| 21 | $C_4F_9CH_2CH_2OH$ | NaB(OCH$_2$CH$_2$C$_4$F$_9$)$_4$ | 6.0 | 120-135 | 175 | 5 | 95 | 3 |
| 22 | $C_4F_9CH_2CH_2OH$ | B(OCH$_2$CH$_2$C$_4$F$_9$)$_3$ Bu$_4$NI | 4.0 4.0 | 105 | 60 | 0.2 | 99.8 | 6 |
| 23 | $C_4F_9CH_2CH_2OH$ | B(OCH$_2$CH$_2$C$_4$F$_9$)$_3$ LiI | 4.0 4.0 | 120 | 75 | 2 | 98 | 5 |
| 24 | $HCF_2CF_2CH_2OH$ | NaB(OCH$_2$CF$_2$CF$_2$H)$_4$ | 6.0 | 120 | 85 | 1.7 | 98.3 | 2 |
| 25 | $HCF_2CF_2CH_2OH$ | B(OCH$_2$CF$_2$CF$_2$H)$_3$ Bu$_4$NI | 4.0 4.0 | 110 | 90 | 0.04 | 99.96 | 5 |
| 26 | $C_3F_7OCHFCF_2OCH_2CH_2OH$ | B(OCH$_2$CH$_2$OCF$_2$CFHOC$_3$F$_7$)$_3$ Bu$_4$NI | 6.0 6.0 | 110 | 100 | 0.5 | 99.5 | 8 |
| 27 | $F(CF_2CF_2CH_2CH_2)_2OH$ | B[O(CH$_2$CH$_2$CF$_2$CF$_2$)$_2$]$_3$ Bu$_4$NI | 4.0 4.0 | 90 | 50 | 1.6 | 98.4 | 6 |

TABLE 1-continued

| Ex. | Alcohol | Catalyst | Catalyst mole % | Temp. °C. | Initial Pressure psig | Unreacted alcohol, % | Alcohol Conversion, % | EO# |
|---|---|---|---|---|---|---|---|---|
| 28 | 1-octanol | B[O(CH$_2$)$_7$CH$_3$]$_3$ | 4.0 | 120 | 100 | 6 | 94 | 2-3 |
|   |   | Bu$_4$NI | 4.0 |   |   |   |   |   |
| 29 | 1-octanol | NaB[O(CH$_2$)$_7$CH$_3$]$_4$ | 6.0 | 110 | 90 | 13 | 87 | 3 |
|   | 1-propanol (5:1 EO:PrOH) | B(OCH$_2$CH$_2$CH$_3$)$_3$ | 4.0 | 110 | 110 | 0.5 | 99.5 | 6 |
| 30 |   | Bu$_4$NI | 4.0 |   |   |   |   |   |
| 31 | 1-propanol (7:1 EO:PrOH) | B(OCH$_2$CH$_2$CH$_3$)$_3$ | 4.0 | 110 | 110 | <0.5 | >99.5 | 7 |
|   |   | Bu$_4$NI | 4.0 |   |   |   |   |   |
| 32 | p-CH$_3$OC$_6$H$_4$OH | B(OC$_6$H$_4$OCH$_3$)$_3$ | 4.0 | 90 | 50 | 1.1 | 98.9 | 3-4 |
|   |   | Bu$_4$NI | 4.0 |   |   |   |   |   |
| 33 | C$_6$H$_5$OH | B(OC$_6$H$_5$)$_3$ | 4.0 | 110 | 125 | <0.1 | >99.9 | 7 |
|   |   | LiI | 4.0 |   |   |   |   |   |

Example 34

C$_6$F$_{13}$CH$_2$CH$_2$OH Ethoxylation Without Catalyst Isolation

A reactor was charged with C$_6$F$_{13}$CH$_2$CH$_2$OH (12 molar equivalents) and boric oxide (B$_2$O$_3$, 1 molar equivalent, corresponding to 2 molar equivalents of boron). The mixture was heated to 80° C. while stirring and sparging with a stream of nitrogen. The nitrogen stream was vented to an ice-cooled trap where water was observed to collect. After 3 h the boric oxide dissolved, and water collection ceased, giving a clear, colorless solution. Karl-Fischer titration analysis of an aliquot showed 100 ppm water content. An aliquot was removed from the solution and analyzed by $^1$H NMR (CDCl$_3$) which showed a 3:1 molar mixture of C$_6$F$_{13}$CH$_2$CH$_2$OH to B(OCH$_2$CH$_2$C$_6$F$_{13}$)$_3$, confirming quantitative conversion of B$_2$O$_3$ to the ester.

To the resulting solution was added 0.6 molar equivalents of NaI and an additional 24 molar equivalents of C$_6$F$_{13}$CH$_2$CH$_2$OH. 117 molar equivalents of ethylene oxide was added (EO to C$_6$F$_{13}$CH$_2$CH$_2$OH ratio=9.8) and the reaction heated at 120° C. Rapid pressure drop was observed. When EO consumption was complete the reactor was cooled and the product analyzed by GC, which showed a mixture of ethoxylates with average ethoxylate number of approximately 9 and 0.7% unreacted C$_6$F$_{13}$CH$_2$CH$_2$OH.

Example 35

C$_6$F$_{13}$CH$_2$CH$_2$OH Ethoxylation Without Catalyst Isolation

A reactor was charged with boric oxide (B$_2$O$_3$, 1 molar equivalent), sodium iodide (1 molar equivalent), and C$_6$F$_{13}$CH$_2$CH$_2$OH (17 molar equivalents). The mixture was heated at 80° C. with stirring and sparging with nitrogen. After 30 min Karl-Fischer titration analysis showed 3000 ppm water content. Heating and nitrogen purging was continued for another 60 min, whereupon titration showed the water content had dropped to 12 ppm.

To the resulting mixture was added 7.2 molar equivalents of ethylene oxide. The reactor was heated to 120° C. and held at that temperature until EO consumption was complete. The reactor was cooled and the product analyzed by GC, which showed a mixture of ethoxylates with average ethoxylate number of approximately 6 and 2% unreacted C$_6$F$_{13}$CH$_2$CH$_2$OH.

Comparative Example 3

Ethoxylation with B(ORf)$_3$ in the Absence of Halide: C4VDF Alcohol

A reactor was charged with 0.888 g of B(OCH$_2$CH$_2$CF$_2$CH$_2$C$_4$F$_9$)$_3$ (0.895 mmol based on 80% and 5.7 g of (17.5 mmol) of HOCH$_2$CH$_2$CF$_2$CH$_2$C$_4$F$_9$. Ethylene oxide (5 mL, 0.10 mol) was then added and the reactor heated to 125° C. After heating for 17 hours no pressure drop was noted. After cooling and removal of unreacted ethylene oxide, GC analysis showed only 3% conversion of the alcohol to the 1-mole ethoxylate, with 97% unreacted alcohol remaining.

Comparative Example 4

Ethoxylation with B(ORf)$_3$ in the Absence of Halide: C6 Alcohol

A reactor was charged with a solution of B(OCH$_2$CH$_2$C$_6$F$_{13}$)$_3$ (4.1 mol %) in HOCH$_2$CH$_2$C$_6$F$_{13}$. Ethylene oxide (25 molar equivalents) was added and the reactor heated to 125° C. for 18 hours. After cooling to room temperature and removing unreacted ethylene oxide the solution was analyzed by gas chromatography which showed only unreacted alcohol and no detectable amount of ethoxylate product.

A reactor was charged with a solution of B(OCH$_2$CH$_2$C$_6$F$_{13}$)$_3$ (9.5 mol %) in HOCH$_2$CH$_2$C$_6$F$_{13}$. Ethylene oxide (25 molar equivalents) was added and the reactor heated to 125° C. for 18 hours. After cooling to room temperature and removing unreacted ethylene oxide the solution was analyzed by gas chromatography which showed >95% unreacted alcohol and trace amounts of ethoxylate product.

Comparative Example 5 n-Octanol Ethoxylation with Sodium n-Octylate n-Octanol (1.31 g, 0.010 mole) and 11 mg NaH (0.46 mmole, 4.6 mol %) were combined at room temperature with stirring. Gas evolution occurred immediately and was complete within 5 minutes to give a solution of sodium in octanol. The solution was charged to the ethoxylation reactor described above along with 5 mL (4.4 g, 0.10 mol) of ethylene oxide. The reactor was heated to 100° C. The reaction was complete within 2 h as judged by monitoring the reactor pressure. After cooling to room temperature 5.20 g (91%) of product was isolated. GC analysis showed a mixture of ethoxylates with an average EO number of 6, a polydispersity of 1.07, and 7.8% unreacted alcohol.

Example 36 n-Octanol Ethoxylation with B(O-n-C$_8$H$_{17}$)$_3$ and Bu$_4$NI

The ethoxylation reactor described above was charged with n-octanol (1.30 g, 0.010 mole), Bu$_4$NI (0.148 g, 0.40 mmol, 4 mol %), and B(O-n-C$_8$H$_{17}$)$_3$ (0.159 g, 0.40 mmol, 4 mol %). Ethylene oxide (5.0 mL, 0.10 mol) was added and the reactor was heated to 100° C. Gas uptake was noticeable immediately. The reaction was allowed to proceed overnight whereupon ethylene oxide conversion was complete as judged by monitoring the pressure. After cooling to room temperature 5.47 g (91%) of product was isolated. GC analysis showed a mixture of ethoxylates with an average EO number of 5.5, a polydispersity of 1.04, and 0.1% unreacted alcohol.

This example and Comparative Example 5 demonstrate that ethoxylation catalysts derived from alkali metal alkoxides give ethoxylate products with wider distributions and significantly larger quantities of unreacted alcohol than do the catalysts of the present invention.

Example 37

Ethoxylation of C$_6$F$_{13}$CH$_2$CH$_2$OH at Low Catalyst Loading (0.6 wt %)

NaI (0.016 g, 0.11 mmol, 0.6 mol %) was dissolved in a mixture of 0.16 g of C$_6$F$_{13}$CH$_2$CH$_2$O(CH$_2$CH$_2$O)$_n$OH (average n=4) and 0.49 g of C$_6$F$_{13}$CH$_2$CH$_2$OH. This solution was charged to the ethoxylation reactor as described above together with B(OCH$_2$CH$_2$C$_6$F$_{13}$)$_3$ (0.133 g, 0.6 mol %) and 6.50 g C$_6$F$_{13}$CH$_2$CH$_2$OH (19 mmol total alcohol). The reactor was then charged with 0.08 mol of ethylene oxide (EO: alcohol=4) and heated to 115° C. for 14 h, 125° C. for 8 h, and then to 135° C. for 14 h, whereupon the pressure dropped to 0 psig and EO uptake was judged complete. The reactor was cooled and 9.8 grams of colorless ethoxylate was isolated product. GC analysis showed 5.5 wt % unreacted alcohol, an average EO number of 4, and polydispersity 1.03.

Example 38

Ethoxylation of 2-Chloroethanol

A reactor was charged with 2-chloroethanol (0.805 g, 0.01 mol), Bu$_4$NI (0.148 g, 0.4 mmol), and B(OCH$_2$CH$_2$Cl)$_3$ (0.0997 g, 0.4 mmol). Ethylene oxide (5 mL, 0.1 mol) was added and the reactor was then heated to 100° C. and the pressure rose to 125 psig. After stirring overnight the pressure dropped to 0 psig, indicating complete ethylene oxide consumption. The reactor was cooled and 5.19 of ethoxylate product was collected. The product composition was confirmed by LCMS which showed a mixture of oligomers Cl(CH$_2$CH$_2$O)$_n$OH with n ranging from 1 to 30 and peaking at about n=11.

What is claimed is:

1. A composition comprising a compound MB(OR$^7$)$_x$(X)$_{4-x}$ wherein: R$^7$ is a linear, branched, cyclic, acyclic, or aromatic hydrocarbyl group, optionally substituted, having from 2 to 20 carbon atoms; X is fluoride, bromide, or iodide; M is a cation of the alkali metals Na$^+$, K$^+$, Li$^+$ or a cation of the type R$^2$R$^3$R$^4$R$^5$N$^+$ or R$^2$R$^3$R$^4$R$^5$P$^+$ where R$^2$, R$^3$, R$^4$, and R$^5$ independently are hydrocarbyl groups of 1 to 20 carbon atoms; and x is 1 to 4, with the proviso that when x=4, R$^7$ is a fluorinated alkyl group.

2. The composition of claim 1 wherein x is 1-3.

3. The composition of claim 1 wherein x is 3.

4. The composition of claim 1 wherein X is iodide.

5. The composition of claim 1 wherein R$^2$, R$^3$, R$^4$, and R$^5$ each are alkyl groups of from 1 to 4 carbons.

6. The composition of claim 1 where M is R$^2$R$^3$R$^4$R$^5$N$^+$, and R$^2$, R$^3$, R$^4$, and R$^5$ are each an alkyl group of 1 to 4 carbon atoms.

7. The composition of claim 1 wherein x is 4 and R$^7$ is a linear fluoroalkyl group of the type C$_y$F$_{2y+1}$CH$_2$CH$_2$ where y is an integer from 2 to 20.

8. A process for preparing the composition of claim 2 comprising combining B(OR$^7$)$_3$ and MX in a suitable solvent, wherein the B(OR$^7$)$_3$ and MX are combined in a molar ratio of from about 1:3 to about 3:1.

9. A process for preparing the composition of claim 2 comprising:
   a) combining B$_2$O$_3$ or B(OH)$_3$ with a compound of the formula R$^7$OH in a suitable solvent to form a reaction mixture;
   b) optionally, removing water from the reaction mixture; and
   c) adding a compound of the formula MX to the reaction mixture in a B$_2$O$_3$ or B(OH)$_3$/MX molar ratio of from about 1:3 to 3:1.

* * * * *